US006334092B1

(12) United States Patent
Hashimoto et al.

(10) Patent No.: US 6,334,092 B1
(45) Date of Patent: Dec. 25, 2001

(54) MEASUREMENT DEVICE AND MEASUREMENT METHOD FOR MEASURING INTERNAL QUALITY OF FRUIT OR VEGETABLE

(75) Inventors: Hirotsugu Hashimoto; Toyohiko Aoki, both of Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 0 days.

(21) Appl. No.: 09/316,070

(22) Filed: May 21, 1999

(30) Foreign Application Priority Data

| May 26, 1998 | (JP) | ................................................ | 10-143795 |
| May 28, 1998 | (JP) | ................................................ | 10-147680 |
| May 28, 1998 | (JP) | ................................................ | 10-147681 |
| Jun. 1, 1998 | (JP) | ................................................ | 10-150955 |

(51) Int. Cl.[7] .................................................. G01N 13/00
(52) U.S. Cl. .............................. 702/81; 702/108; 702/85; 702/75; 356/328
(58) Field of Search .................................. 702/19, 22, 27, 702/28, 30–32, 75–77, 80, 81–84, 85, 106, 108, 183, 189, FOR 103, 104, 107, 115–118, 131, 132, 134, 135, 137, 156–173, 170, 171; 250/222.1, 223 R, 559.24; 382/110, 17, 18, 165, 142, 143, 164; 358/106, 107; 356/425, 407, 237, 394, 398, 384, 385, 386, 387; 209/555, 546, 551, 576, 577, 580, 581, 582, 585–587, 939, 558, 539

(56) References Cited

U.S. PATENT DOCUMENTS

| Re. 33,357 | * | 9/1990 | Randall | ................................. | 358/106 |
| 3,747,755 | * | 7/1973 | Senturia et al. | ................... | 209/111.5 |
| 4,735,323 | * | 4/1988 | Okada et al. | ......................... | 209/582 |
| 5,086,879 | * | 2/1992 | Latimer et al. | ........................ | 186/61 |
| 5,125,039 | * | 6/1992 | Hawkins | ................................. | 382/30 |
| 5,139,335 | * | 8/1992 | Lundeen et al. | ...................... | 356/305 |
| 5,141,323 | * | 8/1992 | Kipphan et al. | ...................... | 356/406 |
| 5,166,755 | * | 11/1992 | Gat | ...................................... | 356/419 |
| 5,247,169 | * | 9/1993 | Okada et al. | ......................... | 250/226 |
| 5,546,475 | * | 8/1996 | Bolle et al. | ........................... | 382/190 |
| 5,726,750 | | 3/1998 | Ito et al. | ............................... | 356/244 |
| 5,732,147 | * | 3/1998 | Tao | ....................................... | 382/110 |
| 5,822,068 | * | 10/1998 | Beaudry et al. | ...................... | 356/417 |
| 5,960,098 | * | 9/1999 | Tao | ....................................... | 382/110 |
| 6,069,696 | * | 5/2000 | McQueen et al. | .................... | 356/326 |
| 6,118,521 | * | 9/2000 | Jung et al. | .............................. | 356/73 |
| 6,137,581 | * | 10/2000 | Kimura et al. | ........................ | 356/433 |
| 6,155,489 | * | 12/2000 | Collins, Jr. et al. | ............. | 235/462.01 |

FOREIGN PATENT DOCUMENTS

| 04-104041 A | 4/1992 | (JP) . |
| 06-213804 A | 8/1994 | (JP) . |
| 07-063616 A | 3/1995 | (JP) . |

OTHER PUBLICATIONS

Patent Abstracts of Japan; Pub. No. 06–213804; Pub. Date: Aug. 5, 1994.
Patent Abstracts of Japan; Pub. No. 07–063616; Pub. Date: Mar. 10, 1995.
Patent Abstracts of Japan; Pub. No. 04–104041; Pub. Date: Apr. 6, 1992.

* cited by examiner

Primary Examiner—Marc S. Hoff
Assistant Examiner—Carol S Tsai
(74) Attorney, Agent, or Firm—Kubovcik & Kubovcik

(57) ABSTRACT

A measurement device for measuring an internal quality of a fruit or vegetable with light is intended to be able to obtain the internal quality at higher speed and with accuracy. In the measurement device of the internal quality, transmitted light through the fruit or vegetable is split into a plurality of frequency regions and the measurement device is provided with a plurality of processing circuits for carrying out intensity data calculating operations simultaneously and in parallel for the respective frequency regions.

39 Claims, 11 Drawing Sheets

MEASUREMENT DEVICE AND MEASUREMENT METHOD FOR MEASURING INTERNAL QUALITY OF FRUIT OR VEGETABLE

BACKGROUND OF THE INVENTION

1. Field of the Invention

The present invention relates to an apparatus for measuring the quality, such as internal sugariness or the like, of the greengrocery (fruits and vegetables) such as oranges, melons, watermelons, and so on on a non-destructive basis and, more particularly, to a processing circuit for processing initial data obtained by the measurement at higher speed and with higher accuracy.

2. Related Background Art

In general, the internal quality of the fruits or vegetables before shipping has been evaluated heretofore mainly by visual inspection of skilled inspectors. Certain fruits or vegetables, if harvested or shipped in a full ripe state, would undergo deterioration of taste, saccharification of sarcocarp, etc. on the market. Therefore, such fruits or vegetables are harvested in an unripe state and thereafter are made to stand under fixed temperature to effect afterripening into an edible state. It was also conventional practice to judge completion of the afterripening by visual inspection of inspectors as above, but it was difficult to make an accurate judgment, because there were no definite criteria for such evaluation of the internal quality of fruits or vegetables.

On the other hand, based on the fact that when near-infrared light is projected onto the fruits or vegetables, such components as sugars, acids, or the like in the fruits or vegetables absorb light of specific wavelengths, it is possible to know the internal quality, such as the sugariness or the like, of the fruits or vegetables by analyzing the light transmitted by the fruits or vegetables and there are known methods for determining the internal quality of the fruits or vegetables on a non-destructive basis, using the transmitted light of the near-infrared light.

Specifically, FIG. 13 is an example to show a schematic diagram of a measurement device for measuring the internal quality of the fruits or vegetables. In FIG. 13, inspected objects 5, which are the fruits or vegetables, are conveyed on a conveyor system 10, for example, such as a conveyor or the like, and in that state the internal quality of the inspected objects 5 is measured continuously. First, the existence of an inspected object 5 on the conveyor system is checked by a position sensor 11. Then a light source 1 radiates light having a predetermined frequency region (which will be referred to hereinafter simply as light) toward the inspected object 5 at a predetermined position A on the conveyor system. Among the radiated light, light of certain wavelengths is absorbed by sugars or the like existing in the inspected object 5 and thereafter the light is transmitted by the inspected object 5 to the outside. This transmitted light is measured by a light receiving element 2 and the transmitted light obtained by this measurement is analyzed in a signal processing device 12, thereby permitting us to know the internal quality of the inspected object 5.

In the practical evaluation of the internal quality of fruits or vegetables, however, the light used in the spectral analysis of fruits or vegetables has a wide frequency region and, in order to obtain the accurate internal quality by signal processing in practice, it is necessary to split the frequency region into a plurality of frequency regions and carry out the signal processing for each of the split frequency regions. Conceivable methods for the division and signal processing of the frequency region include methods of 1) and 2) described below.

1) Interference filters, each transmitting only light in a predetermined frequency region, are prepared in the number of their frequency regions equal to the number of split measurement frequency regions, the filters are continuously changed one by one at a light receiving portion of the light receiving element, so as to continuously send the transmitted light of the split frequency regions to the signal processing device, and the signal processing device carries out the signal processing therewith. One measurement operation for the measured frequency region is completed after the filters all have passed the light receiving portion.

2) For example, as described in Japanese Laid-open Patent Application No. 7-22984, a diffraction grating for separating measured wavelengths is placed at the light receiving portion, the transmitted light after split is guided to an array having storage-type sensors in the number according to the number of separate regions, and after completion of one measurement, data stored is successively subject to signal processing by a single signal processing circuit (including an amplifier etc.).

Since the permissible time for the evaluation of quality in a grading process of fruits or vegetables is very short, the evaluation of fruits or vegetables under conveyance on the conveyor system has to be carried out continuously for the fruits or vegetables. However, since the internal quality of the fruits or vegetables varies considerably, depending upon measured regions thereof, the evaluation has to be carried out on a basis as continuous and in a range as wide as possible. For the accurate evaluation, sufficient light energy has to be accumulated with reception of the transmitted light.

In the case of the method of 1) described above, however, since the fruit or vegetable moves during switching of the interference filters, the measured regions are also shifted with the switching of the frequency regions and data for one frequency region out of the split frequency regions is discontinuous and partial in the measured region on the fruit or vegetable. Further, since the data obtained for the respective split frequency regions is one at different measured regions for the same reason, it is difficult to obtain the accurate measurement result of internal quality. The measurement time for each split frequency region becomes shorter and shorter as the number of split frequency regions increases. This would pose a problem that it is difficult to obtain the sufficient light energy of the transmitted light or the like.

In the case of the method of 2) described above, though the diffraction grating splits the transmitted light at one time, the data stored has to be sent serially from the array to the signal processing circuit. Therefore, data storage start times and storage end times for the respective split frequency regions are shifted in order according to the data transfer times. Since this temporal deviation in the data storage timing for each split wavelength is as small as ten and several msec, the problem of discontinuous measured regions on the fruit or vegetable or different measurement positions of data obtained for the respective split frequency regions, and the problem of decrease in the light energy stored per unit time are not so serious as compared with the case of the method of 1). This method was, however, inadequate in a sense of obtaining a more accurate measurement result of the internal quality of fruit or vegetable or in a sense of decreasing the permissible time for the measurement of quality. Further, this method needs a step of initialization to erase the data stored in each sensor on the array after completion of one measurement. This posed a problem in decreasing the time necessary for the measurement.

In the method 2) described above, a conceivable means for solving the above problem is an approach for increasing the storage time for each frequency region to several ten msec. In this approach, however, if during a certain period within the storage time abnormal intensity data appeared, for example, due to reception of external light other than the transmitted light on the light receiving element or due to the dust or the like attached to the fruit or vegetable, it was difficult to find out a profile of intensity data in the storage time and there was a possibility that the data including the abnormal value was used as it is.

Actual intensities of the transmitted light vary large depending upon the frequency regions and it is thus necessary to select an appropriate amplification factor on the occasion of the signal processing of stored data, set a base line according to the amplification factor, and then carry out the signal processing for calculating the internal quality. With decreasing the storage time, the number of signal processing operations and the number of initialization operations of each sensor also increased, which would raise the possibilities of increase of measurement errors caused by generation of heat due to increase of loads on the signal processing circuit and increase of the measurement time over the permissible time.

Further, in the practical evaluation of the internal quality of fruit or vegetable, the intensity of light through the inspected object 5 is very weak and it is thus necessary to eliminate influence of the external light except for the transmitted light present around the light receiving element 2. For that reason, the measurement system was placed in an unrepresented shield chamber capable of sufficiently intercepting the light from the outside of the apparatus. Further, a disk 8 having cutouts at a predetermined period on the circumference was located between the light source 1 and the inspected object 5, and the disk 8 was rotated by a motor 9 to change the light to pulsed light having the predetermined period. Then the signal processing was carried out with only the pulsed light, thereby eliminating the influence of external light.

In some cases, when the light radiated toward the inspected object 5 is received by the light receiving element 2, it includes not only the transmitted light passing through the inside of the inspected object 5, but also the other light than the transmitted light, resulting from reflection from other inspected objects conveyed before and after the inspected object 5 of interest or resulting from scattering, reflection, etc. due to the dust floating in the measurement system and particles etc. carried into the measurement system by the inspected objects 5 (such light will be referred to hereinafter as stray light). In order to eliminate this influence, the conventional countermeasures contemplated include a method for accommodating the inspected object 5, for example, in a bored shield basket and receiving the transmitted light through the bore, and the like.

The evaluation, however, has to be carried out with effecting high-speed conveyance in order to raise the efficiency of the evaluation of internal quality of fruits or vegetables, and the time necessary for the evaluation has to be decreased thereby. In this case, where the pulsed light is obtained by the aforementioned method, for example, stable operation of the motor 9 is required, but there is the limit in increasing the number of rotations. Even if the pulsed light is obtained by another method, the energy of the light received by the light receiving element 2 will be decreased because of the conversion to the pulsed light. It is, therefore, necessary to increase the energy of the light received in order to obtain the evaluation result with high accuracy.

Further, there recently also occurred some cases where it was difficult to receive the light in sufficient energy for obtaining the intensity data in order to know characteristics of the object unless non-pulsed light was used, depending upon the measured substance of the internal quality. In order to eliminate the influence of the external light without use of the pulsed light, it is effective to enhance the shield performance of the apparatus from the external light, but it increases the size of the apparatus. Therefore, there is the practical limit. Further, the stray light reaching the light receiving element could also increase if the intensity of the light radiated were increased in order to increase the energy of light.

In the actual measurement the internal quality of fruit or vegetable differs greatly depending upon measured regions, and the evaluation of internal quality thus has to be carried out in an area as large as possible. The size of the fruits or vegetables, however, differs considerably even in a single kind. It is thus preferable in practice to carry out the evaluation of internal quality with changing the measurement area according to each inspected object. The enlargement of the measured portion, however, could also increase the influence of the stray light at the same time.

A method for increasing the light energy is one for, with enhancing the shield state of the apparatus from the external light and increasing the intensity of radiated light, for example, splitting the transmitted light into a plurality of frequency regions by the diffraction grating or the like, receiving the transmitted light thus split, using storage-type line sensors or the like as light receiving elements, and, after a lapse of a predetermined time, obtaining the evaluation result by use of the stored data. This method can also further decrease the influence of the external light which has already been weakened by carrying out the initialization of each sensor every appropriate measurements. This method, however, would raise the possibility that when the light receiving element receives instantaneous stray light due to the particles or the like as described above, data is stored also including the stray light, thus failing to obtain an accurate evaluation result.

Even with use of the bored shield basket, the shape of fruits or vegetables is not fixed and it is thus difficult to completely eliminate the gap between the hole of the shield basket and the fruits or vegetables. This becomes more prominent in the case of high-speed conveyance. Therefore, sufficient removal of the stray light cannot be achieved by this method.

Further, in the actual evaluation of the internal quality of fruit or vegetable, the size or absorbance of the inspected objects 5 differs depending upon the individual inspected objects even in the evaluation of the internal quality of fruits or vegetables of a specific kind. It is, however, common practice to determine the internal quality of a fruit or vegetable with the transmitted light through the fruit or vegetable, based on a rate of absorbance of a specific wavelength according to the internal quality in the transmitted light. It is, therefore, possible to evaluate the quality with only the transmitted light from one inspected object and it is virtually possible to derive the evaluation result even if the sizes or transmittances of the individual objects are different.

However, for example, where the fruits are oranges, the differences in the size of the individual oranges, even of a single kind, would cause intensities of the transmitted light to vary by differences of two or more figures in intensity ratios thereof in practice. In general, it is necessary to raise the S/N ratios (ratios of signal to noise) for the accurate intensity analysis every wavelength. It was, however, difficult always to obtain the accurate measurement result of internal quality of all the oranges, i.e., the fruits or vegetables of the same kind, because the differences in the intensities of the transmitted light were too large among the oranges, as described previously.

Further, with a single fruit or vegetable, intensities are also often considerably different among the wavelengths. If a signal amplification factor was set in the signal processing device so as to obtain an accurate measurement result at a specific wavelength accurate evaluation could not be made at wavelengths different from the specific wavelength in certain cases.

In addition, the above-stated evaluation in the grading process of fruits or vegetables normally has to be carried out in a state in which they are conveyed by a conveying system, for example, such as a belt conveyor. In this case, the inspected objects 5 are positioned at random on the belt conveyor and the permissible analysis time for each inspected object is very short. Under such measurement conditions, continuous projection of the near-infrared light from the light source 1 is effective in reducing the measurement time.

In this case, even with consideration to the aforementioned problems related to the signal processing, there, however, occur states in which the inspected object 5 is absent between the light source 1 and the light receiving element 2 during the conveyance, so that the near-infrared light is received directly by the light receiving element 2. As a consequence, there arose the possibility that the base line (a value as a reference of measurement) varied of measured values of the signal processing device 12 connected to the light receiving element 2 or that the signal processing performance was degraded by increase of the temperature or the like in the internal circuits of the signal processing device 12 because of occurrence of too large voltage.

SUMMARY OF THE INVENTION

In order to accomplish an object of the present invention to provide a measurement device of internal quality capable of measuring the internal quality at high speed and with high accuracy, the measurement device of internal quality of fruit or vegetable according to the present invention is a measurement device for measuring an internal quality of a fruit or vegetable, which comprises conveying means for conveying the fruit or vegetable in a predetermined direction, a sensor for checking the existence of the fruit or vegetable under conveyance, light projecting means for projecting light having a predetermined frequency region to the fruit or vegetable, light receiving means for receiving light having been transmitted by the fruit or vegetable, a received signal processing circuit for calculating intensity data according to the transmitted light received by the light receiving means, and an internal quality calculating circuit for calculating the internal quality of the fruit or vegetable by use of the intensity data, wherein the light receiving means has frequency region splitting means for splitting the light having the predetermined frequency region into a predetermined number of frequency regions and the received light processing circuit comprises a plurality of received light processing circuits in a number according to the predetermined number.

As described above, the measurement device for measuring the internal quality of fruit or vegetable is arranged to split the transmitted light received by the light receiving means into the predetermined number of frequency regions, for example, by a diffraction grating or the like and further calculate the intensity data according to the respective split regions simultaneously by the plurality of received signal processing circuits according to the predetermined number of the individual split frequency regions. This permits the measurement to be carried out throughout all the frequency regions at each of continuous measurement resions, even in the measurement in the conveying state, and the accurate analysis of the internal quality of fruit or vegetable can be performed without the discontinuity of measurement regions caused by occurrence of deviation of measurement regions with time and without the initialization of the light receiving portion every measurement.

Since the transmitted light of all the split regions is processed at the same time, no deviation occurs in the measurement region and the light energy used as data per unit time can be made larger than in the case of the storage-type sensors described in the conventional technology being used. This enables more accurate evaluation of the internal quality of fruit or vegetable accordingly. Further, in the structure of the present invention, it is easy to increase the number of split frequency regions if higher-accuracy measurement is demanded or to decrease the number of split frequency regions if low accuracy is accepted. It is also possible to employ a configuration to vary the number of split regions with the device in operation according to the size of the inspected objects or the measurement conditions or the like.

The method using the storage-type sensors could cause the delay of the measurement time and the deviation of the measurement position, as described above. However, for example, where the internal quality measurement device of the present invention is applied to research and development and the like permitting a relatively long measurement time, the aforementioned storage-type sensor array normally permits the frequency region to be split into very fine regions and the measurement method using it is useful. Particularly, an approach to set the storage time of each frequency region to as short as several msec and measure the internal quality of fruit or vegetable in the finely divided ranges permits us to know the quality of fruit or vegetable more accurately and to obtain the aforementioned profile of intensity data and is thus considered to be useful, particularly, in the application to research and development or the like.

According to the present invention, in the case of the storage-type sensors being used, because the measurement device has the received signal processing circuits arranged in parallel, it is also possible to carry out the signal processing and initialization in a quasi-parallel manner by successively sending the stored data to the received signal processing circuits without waiting for the signal processing for each frequency region. Accordingly, even in cases where the number of split frequency regions is set large by use of the storage-type sensor array comprised of a lot of light receiving elements and where the storage time for each of the frequency regions is set to as short as several msec, an actual increase of the measurement time is very small. In addition, the measurement device also presents the effects of decreasing the deviation amount of the measurement position and increasing the transmitted light energy received per unit time, as above.

The frequency region splitting means for splitting the light into the predetermined number of frequency regions can be used in combination with the light receiving means such as a spectroscope and a photosensor, and the light receiving means can be a CCD sensor or the like. Namely, the light receiving means and frequency region splitting means do not have to be discriminated particularly depending upon use, but they can be substantiated by any configuration capable of generating a plurality of electric signals by the function to split the transmitted light into the predetermined number of frequency regions and the function to convert optical energy to electric signals.

The above-stated structure is effective in obtaining the sufficient energy without occurrence of the deviation of measurement position, but no consideration is given to the intensity data not related to the actual internal quality, for example, to the intensity data indicating a singular point on a signal due to the transmitted light itself received, the noise produced in the signal processing operation, and so on. Therefore, when such a singular point seems to have appeared, it is necessary to carry out an operation to find the singular point from the internal quality data finally obtained and remove it, or the like.

In order to accomplish an object of the present invention to provide a measurement device of internal quality having the function to enable the internal quality analysis of fruits or vegetables having different sizes or different absorbances and the internal quality analysis of fruits or vegetables of a single kind with high accuracy, the measurement device of the internal quality of fruit or vegetable according to the present invention is a measurement device of internal quality of fruit or vegetable comprising conveying means for conveying the fruit or vegetable in a predetermined direction, a sensor for checking the existence of the fruit or vegetable under conveyance, light projecting means for projecting light having a predetermined frequency region toward the fruit or vegetable, light receiving means for receiving light having been transmitted by the fruit or vegetable, a received signal processing circuit for converting the transmitted light received by the light receiving means to a voltage signal and calculating intensity data by use of the voltage signal, and an internal quality calculating circuit for calculating the internal quality of the fruit or vegetable by use of the intensity data, wherein the received signal processing circuit continuously calculates the intensity data at intervals of a predetermined time and wherein the internal quality calculating circuit comprises a first memory circuit for storing a plurality of intensity data calculated continuously and a determination circuit for successively comparing the plurality of intensity data stored in the first memory circuit to determine whether the intensity data is to be used for calculation of the internal quality.

As described above, the measurement device of internal quality of fruit or vegetable according to the present invention does not adopt the method for removing the influence of external light by use of the pulsed light. An improvement in the shield state and a decrease in reception of the stray light are accomplished by improving the structure of the apparatus and employing such structure that the projected light is parallel light and the light receiving means is provided with a shield cylinder being coaxial with the parallel light and having one open end in contact with the light receiving means and the other open end as close to the fruit or vegetable as possible. At the same time, the initialization is effected for each sensor every appropriate measurements, thereby further removing the influence of the external light. Further, as to the stray light, the determination circuit determines whether the intensity data obtained includes an abnormal value due to the stray light and if the data includes an abnormal value it is corrected to eliminate the influence thereof.

In general, the influence due to the stray light is often instantaneous. (The stray light can be eliminated by correction of the base line or the like on the occasion of the initialization of sensors or the like if it is received continuously by the light receiving elements.) For example, when the intensity data is recorded in the time duration of several msec with the transmitted light of a predetermined wavelength, the intensity data as illustrated in FIG. 7 is recorded. The intensity data is stored in the first memory circuit per unit time and the determination circuit successively performs comparison with preceding and succeeding data. With the intensity data determined as an abnormal value at this stage, a proper arithmetic operation is carried out to obtain a value that can be approximated from the preceding and succeeding intensity data and it is stored as intensity data after correction, together with the normal intensity data stored in the first memory, into the second memory. The above operation eliminates the influence of the stray light considerably.

Further, the intensity data stored in the second memory is used in such a manner that it is integrated to calculate the internal quality and on that occasion the number of integrations of the intensity data is varied according to the diameter of the fruit or vegetable preliminarily measured. This always adjusts the measurement area of each fruit or vegetable to a range according to the size of the fruit or vegetable, thereby enabling accurate calculation of the internal quality. Namely, this obviates the need for re-calculation using the comparison data of the size of fruit or vegetable and the like, thereby enabling great reduction of the time necessary for the evaluation of internal quality.

The integration time can also be calculated from the size of the fruit or vegetable as described above or from an intensity ratio of the transmitted light of a predetermined frequency. Specifically, the measurement device may be arranged to determine a change of the measurement area due to the size of each fruit or vegetable from an attenuation amount of the transmitted light as to the transmitted light through each fruit or vegetable and use only a portion to present a proper attenuation amount.

In order to increase the calculation speed of the intensity data, the measurement device may be arranged so that the transmitted light is split into a plurality of frequency regions, the device is provided with a plurality of received signal processing circuits corresponding to the respective split frequency regions, and the calculation of intensity data is carried out simultaneously from the transmitted light thus split, in the respective received signal processing circuits. In this case, the determination of an abnormal value, the correction operation, etc. may be carried out, not only with the preceding and succeeding intensity data but also among the frequency regions. It is noted that the alteration of the integration time or the like does not have to be effected for all the split frequency regions and it can also be contemplated that the measurement device adopts a method for altering the integration time for only a frequency region related to the internal quality to be measured.

Further, in order to accomplish an object of the present invention to provide an internal quality measurement device which enables measurement in short time and with high accuracy, independent of the size of the individual fruits or vegetables in the measurement of the internal quality of specific fruits or vegetables, a non-destructive measurement device of internal quality of fruit or vegetable according to the present invention is a measurement device of internal quality of fruit or vegetable comprising conveying means for conveying the fruit or vegetable in a predetermined direction, a sensor for checking the existence of the fruit or vegetable under conveyance, light projecting means for projecting light having a predetermined frequency region toward the fruit or vegetable, light receiving means for receiving light having been transmitted by the fruit or vegetable, a received signal processing circuit for calculating intensity data according to the transmitted light received by the light receiving means, and an internal quality calculating circuit for calculating the internal quality of the fruit or vegetable by use of the intensity data, wherein the received signal processing circuit comprises a plurality of amplifying circuits having different amplification factors for calculation of a plurality of amplified intensity data and wherein the internal quality calculating circuit comprises a selection circuit for selecting intensity data amplified to predetermined amplitude out of the plurality of amplified intensity data.

As described above, the received signal processing circuit simultaneously calculates the plurality of intensity data at the different amplification factors. Further, the selection circuit provided in the internal quality calculating circuit is arranged to determine the intensity of the intensity data at a wavelength being the reference in each intensity data, select intensity data at the amplification factor so as to present the intensity where the best S/N ratio is obtained in the measurement device, and calculate the internal quality of the fruit or vegetable, using this intensity data selected. Therefore, the measurement result of the internal quality can always be obtained based on the stable S/N ratio.

At the same time, by employing the structure in which the plurality of intensity data at the different amplification factors is calculated simultaneously and the predetermined intensity data is selected from the intensity data after the calculation, the measurement device has the effects of such advantages that it is easy to increase or decrease the number of amplified intensity data and that the time necessary for the amplification and selection in that case is not so dependent on the number of intensity data. In the present embodiment the light intensity range is divided into only two levels, a low level and a high level, but the number of divided levels should preferably be changed according to characteristics of the inspected objects and operating circumstances of the measurement device.

Further, in order to increase the light energy of the transmitted light and eliminate the temporal deviation of the measured portion, the measurement device may also be arranged to split the transmitted light into a plurality of frequency regions, be provided with a plurality of received signal processing circuits corresponding to the respective split frequency regions, and calculate the intensity data simultaneously from the transmitted light thus split, in the respective received signal processing circuits. The present invention is effective, particularly, in cases where the decrease of the time necessary for the calculation of internal quality after reception of the transmitted light is demanded, as in the above case where the light is split into the frequency regions.

In the above-stated structure, in order to be ready for large intensity differences among the wavelengths in the frequency region of the transmitted light through a single fruit or vegetable, it is preferable to employ a configuration in which the transmitted light is split into a plurality of frequency regions and the measurement device is provided with a plurality of amplifying circuits having different amplification factors for each of the split regions. This configuration enables the device to amplify and process the transmitted light in the frequency region with relatively large intensity and the transmitted light in the frequency region with relatively small intensity, at the optimum amplification factor within the shortest processing time. It is noted that the plurality of amplifying circuits do not always have to be provided for all the split frequency regions, but the measurement device may also be constructed in such structure that the plurality of amplifying circuits are provided for only a frequency region associated with the internal quality to be measured.

Further, in view of the aforementioned problem in the state in which the inspected object 5 is absent between the light source 1 and the light receiving element 2, another object of the present invention is to provide a measurement device of internal quality of fruit or vegetable which enables the measurement of the internal quality with high accuracy even in the conveying state of the inspected object, overcoming the problem of degradation of the signal processing performance due to the deviation of initial setting of the signal processing device 12, the occurrence of too large voltage, or the like even in the absent state of object.

For accomplishing the above object, a measurement device of internal quality of fruit or vegetable according to the present invention is a non-destructive measurement device of internal quality of fruit or vegetable comprising conveying means for conveying the fruit or vegetable in a predetermined direction, a sensor for checking the existence of the fruit or vegetable under conveyance, light projecting means for projecting light having a predetermined frequency region toward the fruit or vegetable, light receiving means for receiving light having been transmitted by the fruit or vegetable, a received signal processing circuit for calculating intensity data according to the transmitted light received by the light receiving means, and a calculating circuit for calculating the internal quality of the fruit or vegetable by use of the intensity data, wherein the received signal processing circuit comprises a signal converting circuit for converting the transmitted light to a voltage signal, a comparator circuit for comparing the voltage signal with a predetermined voltage value to determine whether the voltage signal is larger than the predetermined voltage value, a voltage signal switching circuit for sending the voltage signal to an amplifying circuit when the voltage signal is smaller than the predetermined voltage value and sending a predetermined reference voltage to the amplifying circuit when the voltage signal is larger than the predetermined voltage value, an amplifying circuit for amplifying the voltage signal, and a calculating circuit for calculating intensity data from the voltage signal amplified.

As described above, in the received signal processing circuit, the transmitted light is converted to the voltage signal by the signal converting circuit and the voltage signal is amplified by the amplifying circuit to be used for the calculation of intensity data. When the fruit or vegetable is present between the light projecting means and the light receiving means, the comparator circuit determines that the voltage signal is smaller than the predetermined voltage value and the voltage signal is sent to the amplifying circuit to be used for the calculation of the intensity data as it is.

When the fruit or vegetable is absent between the light projecting means and the light receiving means, it is determined that the voltage signal is larger than the predetermined voltage value and the predetermined reference voltage is sent to the amplifying circuit by the voltage signal switching circuit. The above operation eliminates the occurrence of too large voltage in the received signal processing circuit, thereby preventing the deviation of initial set value and the degradation of the signal processing performance.

Further, the measurement device may also be arranged to carry out the initial setting of the light receiving means or the inspection of the light projecting means every measurement, based on the comparison between the predetermined voltage value and the voltage signal obtained when the fruit or vegetable is absent between the light projecting means and the light receiving means. With the predetermined reference voltage sent to the amplifying circuit when the fruit or vegetable is absent between the light projecting means and the light receiving means, the initial setting may also be carried out for variables in the calculation of intensity data or for variables in the calculation of internal quality in the CPU or the like.

In order to obtain the measurement result of internal quality with higher accuracy, it is preferable to split the transmitted light into a predetermined number of frequency regions, provide the measurement device with received signal processing circuits corresponding to the respective split frequency regions, and calculate the intensity data simultaneously by the plurality of received signal processing circuits. In that case, each received signal processing circuit can be arranged to include the comparator circuit etc. described above or only a received signal processing circuit corresponding to a specific frequency region can also be arranged to have the comparator circuit etc. described above.

DETAILED DESCRIPTION OF THE PREFERRED EMBODIMENTS

Figure 1:
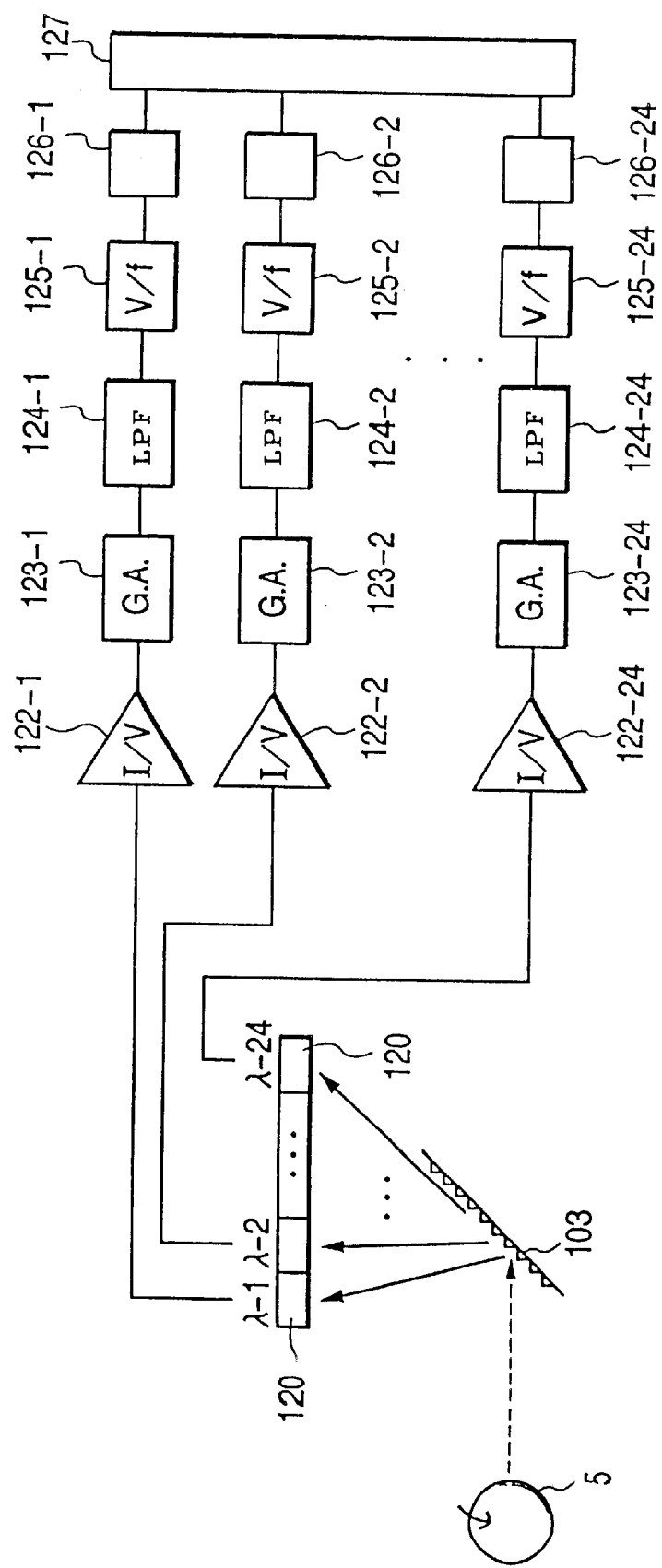
FIG. 1 is a block diagram to illustrate signal processing associated with a first embodiment of the present invention.

FIG. 1 is a block diagram to show the signal processing associated with the first embodiment of the present invention. The present embodiment is not different from the conventional technology in the conveyor system 10, the position sensor 11, and the light source 1 and in the path in which the light having the predetermined frequency region (which will be referred to hereinafter simply as light) is emitted from the light source 1 toward the inspected object 5 and in which the light travels through the inspected object 5 and, therefore, the description thereof will be omitted herein. In the present embodiment, the light having been transmitted by the inspected object 5 is split into twenty four frequency regions $\lambda$-1 to $\lambda$-24 by diffraction grating 103 immediately before photodiodes 120. Further, the photodiodes 120 are arranged corresponding to the number of split frequency regions and the transmitted light of the predetermined frequency region is thus measured by the predetermined photodiodes 120. For each photodiode 120, a signal processing routine is carried out in a received signal processing circuit composed of a current-voltage conversion amplifier, a gain amplifier, a low-pass filter, a voltage-frequency converter, and a counter and the signal processing routine is common to all the light receiving elements. Therefore, the signal processing routine will be described as to the case of $\lambda$-1 below. In the present embodiment the number of split regions is twenty four, but the number of split regions should preferably be determined as an appropriate number according to an object to be inspected.

The transmitted light after split is converted to current by the photodiode 120 and the current is further converted into a voltage signal by the current-voltage conversion amplifier 122-1. The voltage signal obtained is amplified by the gain amplifier 123-1 and thereafter noise components are cut by the low-pass filter 124-1. Further, the voltage-frequency converter 125-1 converts the signal to frequency. During a period of predetermined integration time t thereafter, the counter 126-1 counts the frequency. The frequency thus counted is input as intensity data $D-1=f-1\times t$ of the transmitted light $\lambda$-1 projected onto the photodiode 120, into the CPU 127.

Figure 2:
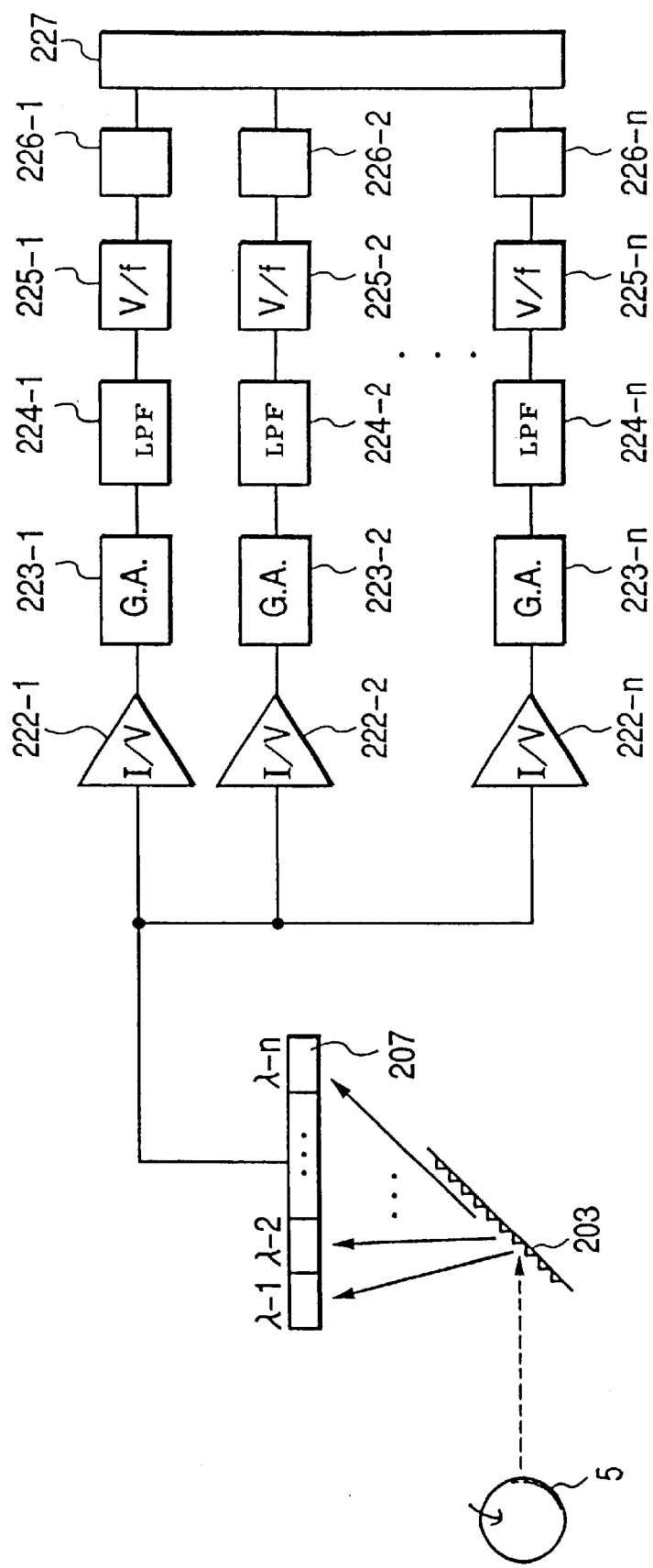
FIG. 2 is a block diagram to illustrate signal processing associated with a second embodiment of the present invention.

Next, a signal block diagram associated with the second embodiment of the present invention is illustrated in FIG. 2. The present embodiment is different from the first embodiment in that a sensor array 207 comprised of a plurality of MOS type image sensors (storage-type sensors) is used instead of the photodiodes 120. In the present embodiment, the light having been transmitted by the inspected object 5 is split into n frequency regions $\lambda$-1 to $\lambda$-n by the diffraction grating 203 immediately before the sensor array 207. The sensor array 207 serially sends charges (stored data) corresponding to the respective split frequency regions to the corresponding current-voltage conversion amplifiers. The signal processing thereafter is the same as in the first embodiment.

Since the present embodiment is arranged to process the stored data serially sent from the sensor array 7 on a quasi-parallel basis, a large increase will not be encountered in signal processing times or in deviation of the measurement position even if optimum gains are selected for the respective stored data. Therefore, the present embodiment has the effect of enabling the transmitted light to be analyzed finely using the MOS type image sensor array which generally has the number of separate channels not less than several hundreds. If the sensor array 207 is arranged to be capable of sending the stored charges to the current-voltage conversion circuits coupled in parallel, the present embodiment will also be able to achieve the same effect as the first embodiment.

Figure 3:
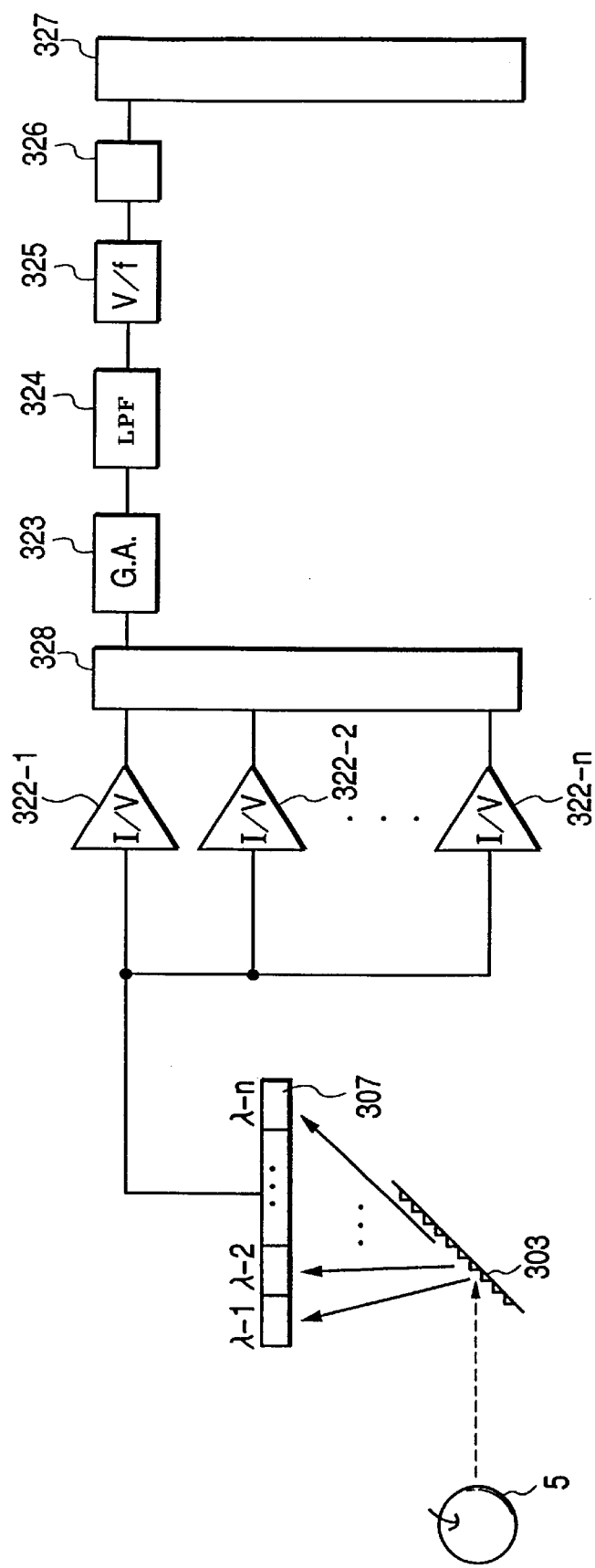
FIG. 3 is a block diagram to illustrate signal processing associated with a third embodiment of the present invention.

The second embodiment employed the structure having the received signal processing circuits in the number corresponding to the number of split regions, but the structure including a plurality of gain amplifiers and after is not practical, because the total production cost of the received signal processing circuits increases greatly. The third embodiment is thus constructed in such structure as illustrated in the signal block diagram of FIG. 3 in which the charges corresponding to the respective frequency regions are converted to voltage signals by the corresponding current-voltage conversion amplifiers and thereafter the voltage signals are transmitted through a multiplexer 328 to a single gain amplifier 323. This presents the same effect as in the second embodiment without largely increasing the production cost.

Further, if the third embodiment is arranged to enable the sensor array 307 to send the stored charges to the current-voltage conversion circuits coupled in parallel, the timing of multiplexing with placement of the multiplexer 328 will not be limited to after the current-voltage conversion, but may also be set to after the amplification of signal which necessitates the longest processing time. This arrangement can achieve the effect almost similar to that in the first embodiment.

The intensity data input into the CPU 127, 227, or 327 is converted to internal quality data through a predetermined arithmetic operation and these are displayed in the form of an image on a CRT or the like. The image display may also be of a type of displaying only the propriety of shipping time of the inspected object 5 with respect to the reference of a predetermined sugariness. Further, the apparatus may also be arranged to output only the propriety data without any image display and carry out grading of inspected object 5 in the conveyor system continuous from the measurement device.

Execution of the present invention enables the data processing and analysis of the transmitted light through the fruit or vegetable to be carried out within a much shorter time than the processing time in the conventional technology and also enables the internal quality measurement of the fruit or vegetable to be carried out within short time and with high accuracy.

The structures in the first, second, and third embodiments are effective in terms of obtaining sufficient light energy without occurrence of deviation in the measurement position, as described above. However, if there is intensity data not related to the actual internal quality, for example, intensity data indicating a singular point on a signal due to the transmitted light itself to be received or the like, it is necessary to carry out processing to find the singular point from the internal quality data obtained finally and to remove it or the like.

The fourth and fifth embodiments will be described below in structure including the arrangement for removing the singular point appearing on the signal.

Figure 13:
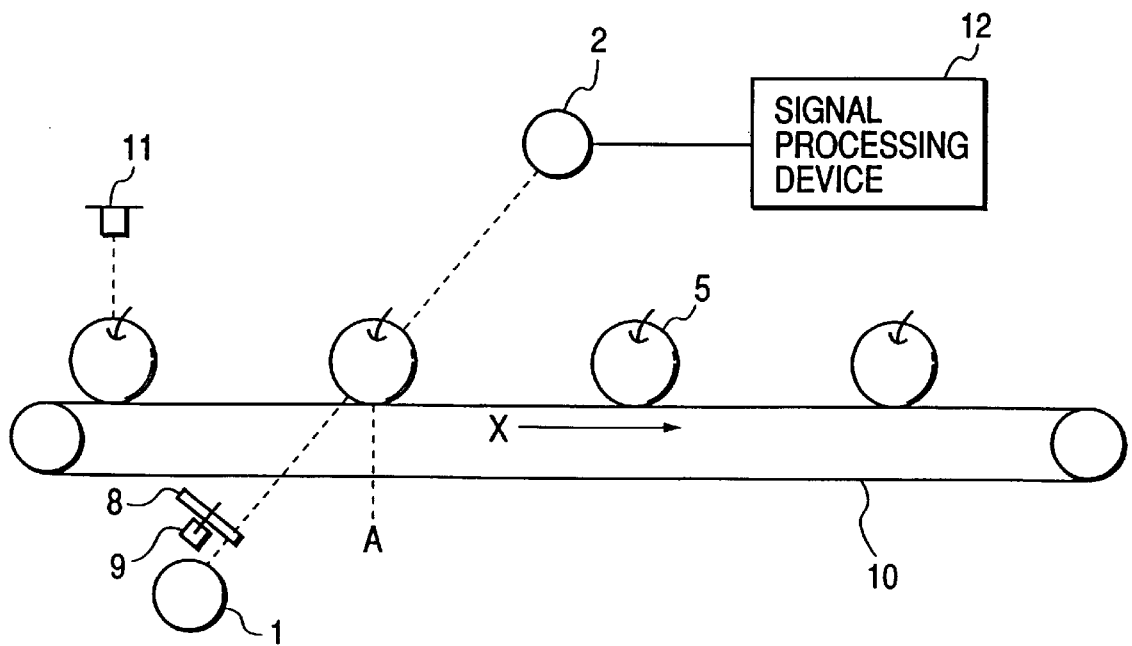
FIG. 13 is a diagram to show the schematic structure of an internal quality measurement device of fruit or vegetable using light having a predetermined frequency region in the conventional technology.

The schematic structure of the measurement device of internal quality of fruit or vegetable associated with the fourth embodiment of the present invention is such that the disk 8 and motor 9 are excluded from the conventional example illustrated in FIG. 13 and a shield cylinder is added instead. A position sensor 11 is provided in order to check the existence of inspected object 5 and measure the diameter of inspected object 5. Further, the diffraction grating 403 is located immediately before the light receiving unit 2 and the light receiving unit 2 is a sensor array composed of a plurality of photodiodes 420. The other components, i.e., the conveyor system 10, the light source 1, and the signal processing device 12 including the received signal processing circuits and the internal quality determining circuit, are the same as in the conventional example.

The light source 1 emits the light having the predetermined frequency in the form of parallel light toward the inspected object 5. There is the shield cylinder coaxial with the parallel light and in contact with the light receiving unit 2 between the inspected object 5 passing the position of A and the light receiving unit 2. This shield cylinder permits the light receiving unit 2 to receive only the light traveling straight through the inspected object 5 from the light source 1 to the light receiving unit 2. As a consequence, the influence of external light and stray light can be reduced.

Figure 4:
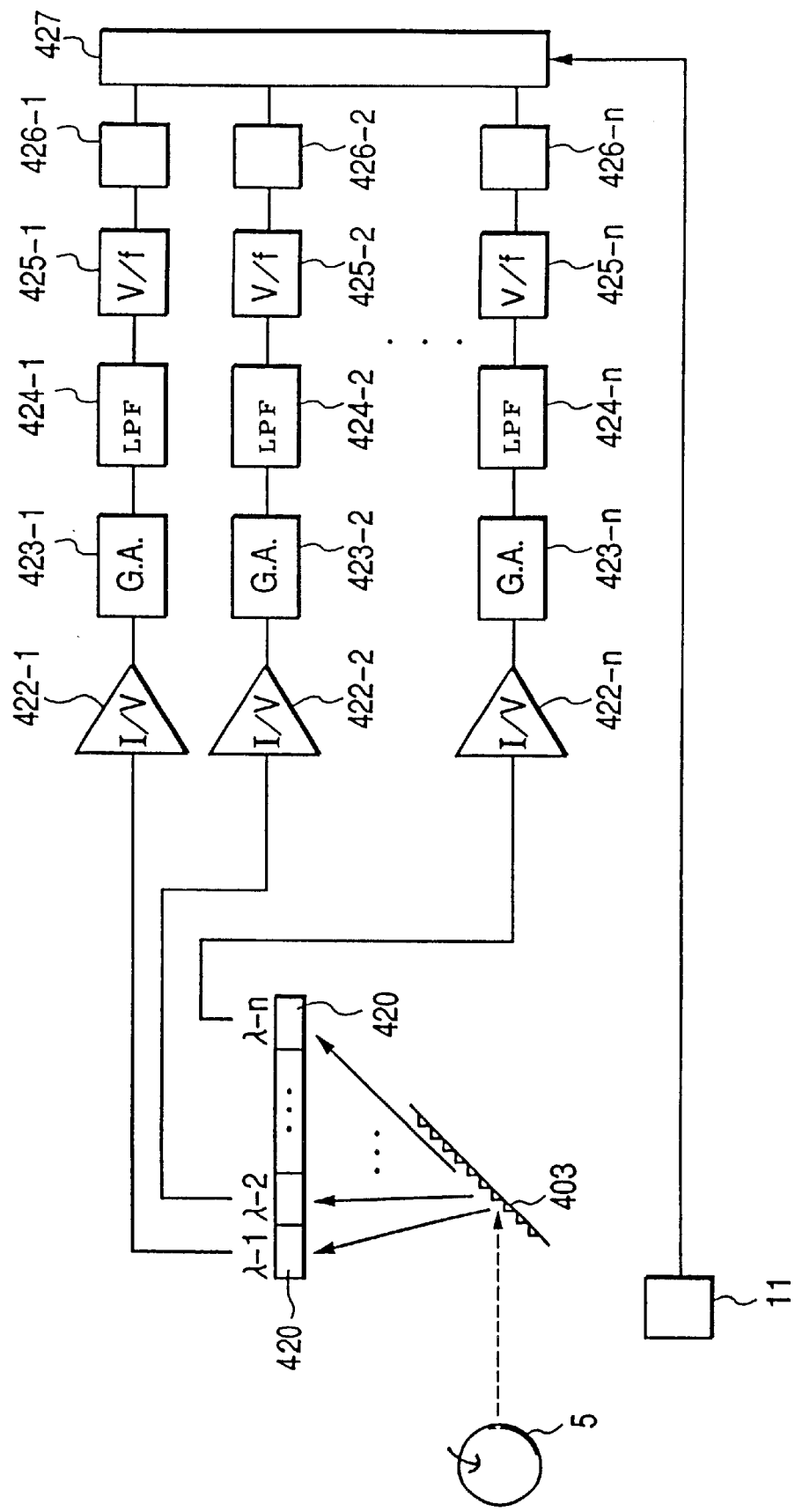
FIG. 4 is a block diagram to illustrate signal processing associated with a fourth embodiment of the present invention.

Next, the block diagram of signal processing in the present embodiment is illustrated in FIG. 4 as to the signal processing after the photodiodes 420 receive the transmitted light. The transmitted light received by the light receiving unit 2 is split into predetermined frequency regions $\lambda$-1 to $\lambda$-n by the diffraction grating 403. The light after split is converted to current signals in the corresponding photodiodes 420 on the sensor array. Since the same signal processing is carried out for the split frequency regions, only one single signal processing circuit will be described below. The current signal from the photodiode 420 is converted to a voltage signal by the current-voltage conversion amplifier 422-1.

The voltage signal obtained is amplified by the gain amplifier 423-1 and thereafter noise components are cut by the low-pass filter 424-1. Further, the voltage-frequency converter 425-1 performs conversion of the signal to frequency and the counter 426-1 performs integration every msec. After that, the signals are successively supplied as intensity data of the transmitted light to the CPU 427 which is an internal quality calculating circuit. The integration time of the counter 426-1 is desirably not more than 1 msec in a sense of judging intensity data momentarily indicating an abnormal value due to the stray light and in a sense of carrying out high-speed conveyance of the inspected object 5.

Figure 5:
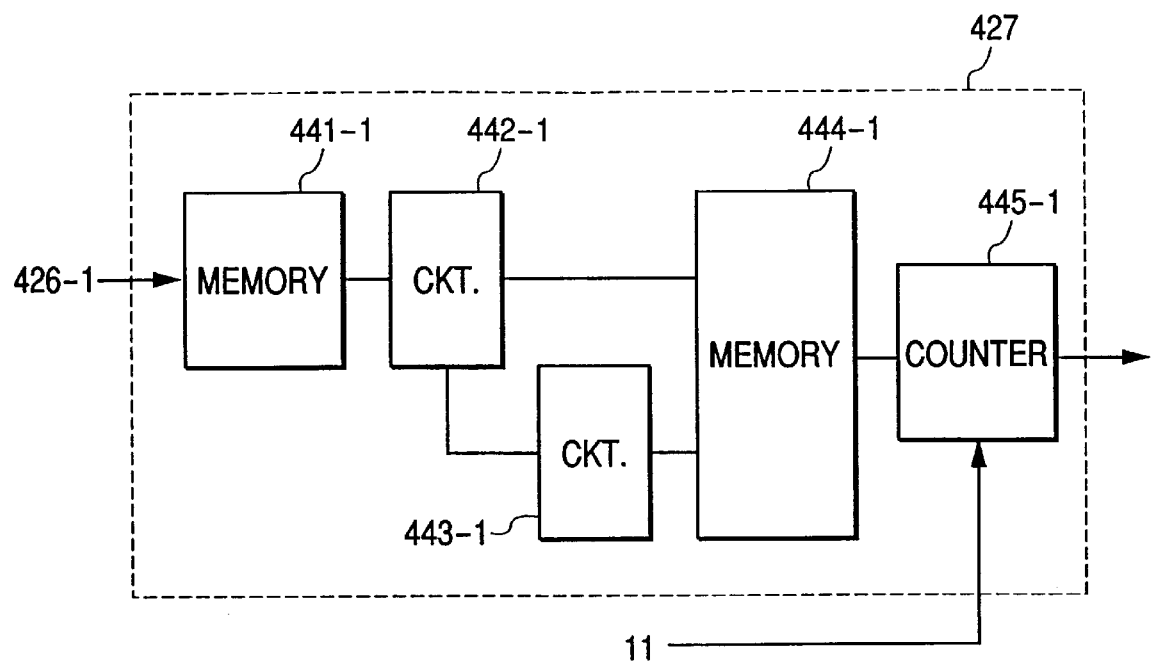
FIG. 5 is a block diagram to illustrate signal processing in CPU 427 associated with the fourth embodiment of the present invention.
Figure 7:
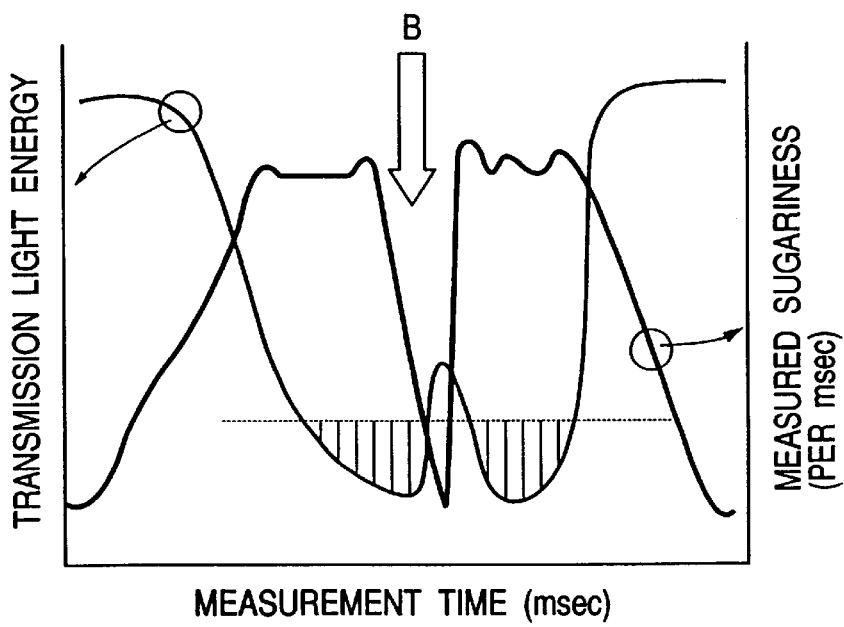
FIG. 7 is a diagram to show a light energy profile including influence of stray light in measurement of internal quality.

A block diagram of signal processing in the present embodiment is illustrated in FIG. 5 as to the signal processing in the CPU 427. The intensity data sent from the counter 426-1 is stored in a first memory 441-1 and a determination circuit 442-1 determines whether there exists data indicating a measurement anomaly as indicated by B in FIG. 7. Intensity data determined as a measurement anomaly by the determination circuit 442-1 is corrected through an appropriate arithmetic operation using intensity data determined as a normal measurement by a correction circuit 443-1. The present embodiment is arranged to carry out the determination and correction based on the intensity data continuous in time series, but the device may also be constructed in such structure as to use or add the determination and correction based on a continuous portion in each of the split frequency regions.

A second memory 444-1 stores intensity data excluding the influence of the stray light, based on the intensity data judged to be a normal measurement and the intensity data corrected. The intensity data is obtained every msec and stored in the second memory 444-1 and an optimum measurement range, i.e., an optimum measurement time, is computed based on the diameter of the inspected object 5 measured by the position sensor 11. Then the intensity data stored according to the measurement time is integrated by counter 445-1, thus carrying out the operation for obtaining the internal quality.

The intensity data input into the CPU 427 is converted to the internal quality data through the predetermined arithmetic operation and these are displayed in the form of an image on the CRT or the like. The image display may also be of the type of displaying only the propriety of shipping time of the inspected object 5 with respect to the reference of a predetermined sugariness. Further, the apparatus may also be arranged to output only the propriety data without the image display and perform the grading of inspected object 5 in the conveyor system continuous after the measurement device.

The fourth embodiment was described as to the example in which the structure for eliminating the singular point on the signal was added to the first embodiment, but it is a matter of course that the same effect as in the fourth embodiment can also be presented where this structure is added to the second and third embodiments. Further, this structure for eliminating the singular point on the signal also exhibits the effect of obtaining an accurate internal quality profile even in the conventional technology, i.e. in the method of successively processing all the split frequency regions of the near-infrared transmitted light by the single received signal processing circuit.

Figure 6:
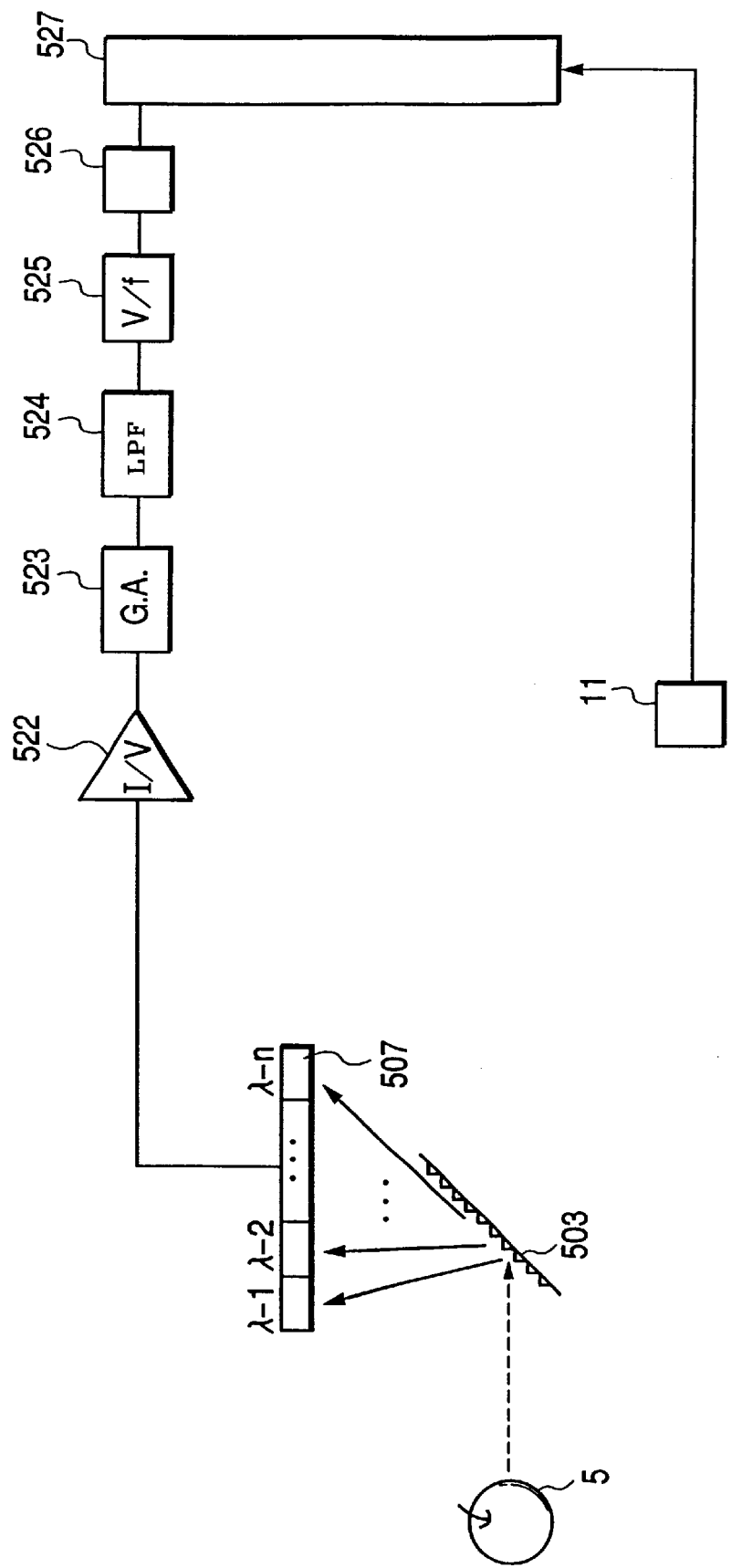
FIG. 6 is a block diagram to illustrate signal processing associated with a fifth embodiment of the present invention.

An embodiment in which the structure for eliminating the singular point on the signal according to the present invention is added to the conventional technology will be described as the fifth embodiment. Therefore, the present embodiment is different from the fourth embodiment in that, as illustrated in FIG. 6, the sensor array 507 composed of a plurality of storage-type sensors corresponding to the respective split frequency regions is used in place of the sensor array composed of the photodiodes 420 and the signal processing circuit comprises a single circuit.

In the present embodiment the stored charges need to be successively sent to the signal processing circuit and, therefore, the integration time in the counter 526 has to be not less than ten and several msec, which makes it difficult for the apparatus to adapt for high-speed conveyance. There also arises the possibility that accurate detection of an abnormal value or correction is hard depending upon the time of occurrence of an anomaly due to the stray light. This would raise the need for monitoring the data of the first memory. The present embodiment, however, has the advantages of the simpler circuit configuration than the fourth embodiment and the capability of increasing the number of channels (the number of split frequency regions) in the storage-type sensor array and is thus suitably applicable as a simple device to application in research and development and the like.

Execution of the present invention enables the device to obtain the data of transmitted light excluding the influence of the stray light where the internal quality of fruit or vegetable is measured at high speed and also enables the measurement of internal quality of fruit or vegetable to be carried out at high speed and with high accuracy.

Figure 8:
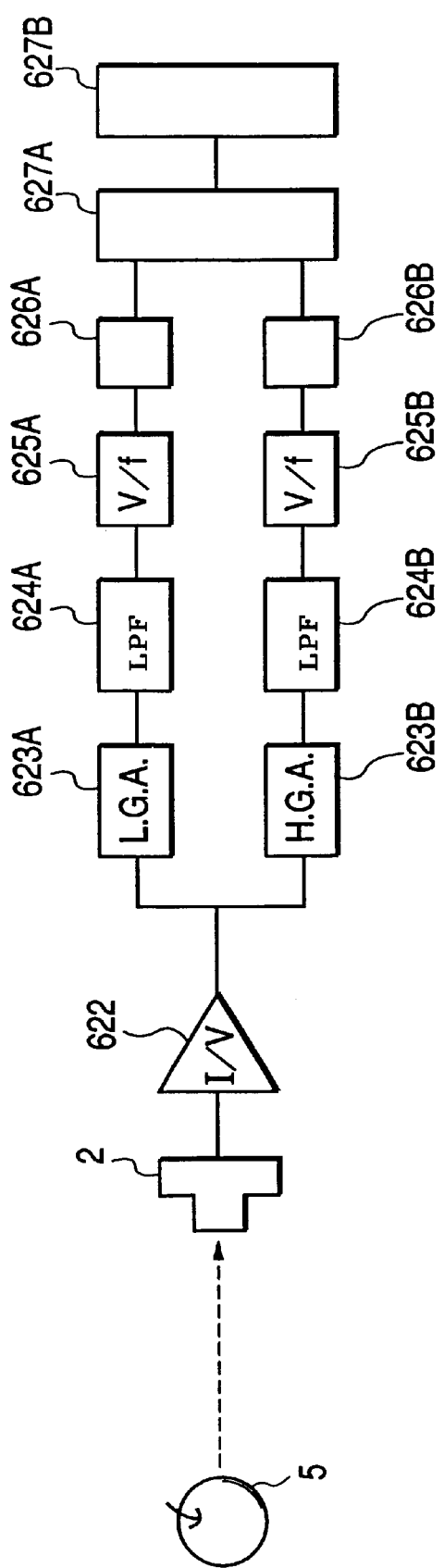
FIG. 8 is a block diagram to illustrate signal processing associated with a sixth embodiment of the present invention.

A block diagram of the signal processing associated with the sixth embodiment of the present invention is illustrated in FIG. 8. The present embodiment is not different from the conventional technology in the structure and the function of each component, including the conveyor system 10, the position sensor 11, the light source 1, the light receiving unit 2 (photodiode), and the path in which the light emitted from the light source 1 toward the inspected object 5 travels through the inspected object 5 and in which the transmitted light is received by the photodiode 2, and the description thereof will be omitted herein. Described below is the signal processing routine of the transmitted light received by the photodiode 2 in the present embodiment.

The transmitted light is converted to current by the photodiode 2 and the current is further converted to a voltage signal by the current-voltage conversion amplifier 622. Further, the voltage signal obtained is sent to each of two types of gain amplifiers 623A, 623B having different amplification factors. The voltage is amplified by the gain amplifier 623A, 623B and thereafter noise components are cut by the low-pass filter 624A, 624B. Further, the voltage-frequency converter 625A, 625B performs conversion of the signal to frequency. After that, the counter 626A, 626B counts the frequency during the period of predetermined integration time t.

The frequencies thus counted are supplied as intensity data of the transmitted light received by the photodiode 2, $DA=fA \times t$ and $DB=fB \times t$, independently and simultaneously to a selection circuit 627A. The selection circuit 627A determines an intensity at only a predetermined reference wavelength in each intensity data DA, DB, selects intensity data nearest to a predetermined signal intensity, and sends the intensity data to the CPU 627B. The CPU 627B calculates the internal quality data of inspected object 5, using the intensity data thus sent.

For example, where the intensity of transmitted light is high, so that the voltage value of the voltage signal after the conversion is large, because the absorbance of the inspected object 5 is small or because the size of the inspected object 5 is small, the selection circuit selects the intensity data DA obtained when the voltage signal is amplified by the low-gain amplifier 623A. Where the intensity of the transmitted light is weak, so that the voltage value of the voltage signal after the conversion is low, because the absorbance of the inspected object 5 is high or because the size of the inspected object 5 is large, the selection circuit selects the intensity data DB obtained when the voltage signal is amplified by the high-gain amplifier 623B.

In the present embodiment the intensity data having the predetermined intensity always undergoes the signal processing in the CPU 627B and, therefore, the accurate internal quality data is obtained based on stable S/N ratios. It is preferable to use two or more types of amplification factors in order to obtain more accurate internal quality data, but in this case, because the selection circuit 627A is arranged to determine only the intensity at the single wavelength, the time necessary for the signal processing is not increased even if the number of gain amplifiers is not two as above but more than it.

The structure associated with the embodiment of the present invention can accomplish the effect of always obtaining the data with stable S/N ratios for each inspected object by adding this structure to the conventional technology, and this was described above as the sixth embodiment. Likewise, this structure also exhibits the same effect where a plurality of received signals resulting from division of the near-infrared light are processed in parallel.

Figure 9:
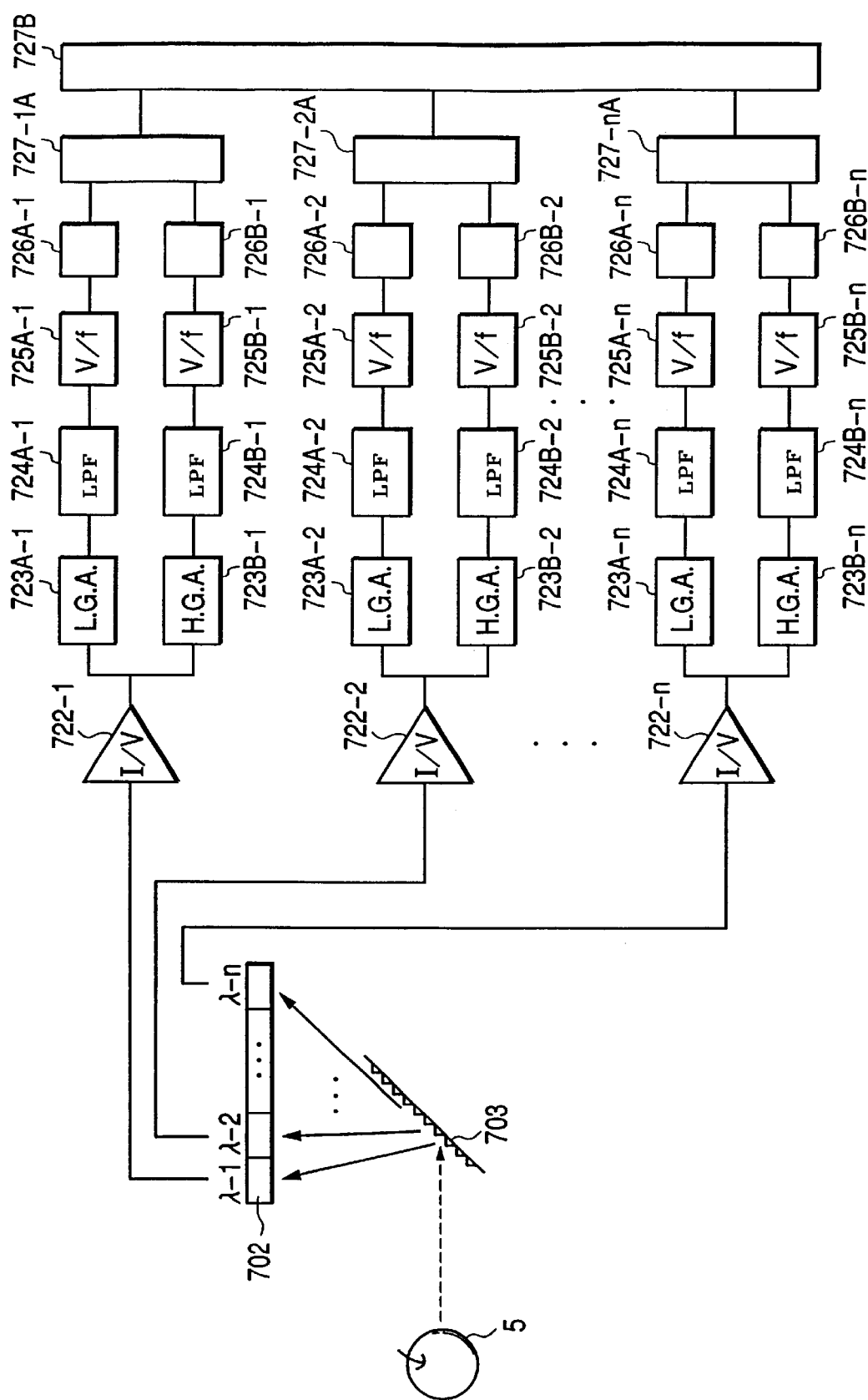
FIG. 9 is a block diagram to illustrate signal processing associated with a seventh embodiment of the present invention.

Then, the seventh and eighth embodiments are constructed as embodiments in which the above-stated structure intended to obtain the stable S/N ratios is added to the structure for processing a plurality of received signals in parallel or in quasi-parallel, which was described in the first and second embodiments, and a block diagram of the signal processing associated with the seventh embodiment is illustrated in FIG. 9. The description of the portions related to the same structure as in the sixth embodiment will be omitted herein and only different portions will be explained.

In the seventh embodiment the light having been transmitted by the inspected object 5 is split into a plurality of frequency regions by the diffraction grating 703. Further, the transmitted light thus split is converted to current by each of photoelectric conversion elements 702 provided in the number equal to the number of split regions and the current is converted to a voltage signal in the corresponding current-voltage conversion amplifier 722-n. The structure for each frequency region has two types of gain amplifiers, i.e. low and high gain amplifiers 723A-n, 723B-n, having different amplification factors and each voltage signal is subjected to the calculation to obtain corresponding intensity data according to the processing similar to that in the first embodiment. It is noted that the apparatus may also be constructed in such structure that the transmitted light after the division is stored as charges in a sensor array, for example, composed of MOS type image sensors (storage-type sensors) and each sensor is coupled to the structure having two types of, low and high, gain amplifiers 723A-n, 723B-n having different amplification factors.

When the internal quality of fruits or vegetables of a single kind is measured, profiles of transmitted light thereof are similar relative to each other. However, in cases where the frequency region is split and the amplification factors are changed every split region, the rate of change is very large and the preferred effect is not achieved in terms of the processing time and the accuracy of intensity data obtained. In the present embodiment the device is constructed in the structure having a plurality of amplifying circuits for each of the split frequency regions whereby the optimum amplification factor is always selected without a large change in the amplification factor every measurement and without a large increase in the processing time, thereby achieving the measurement result with high accuracy.

Figure 10:
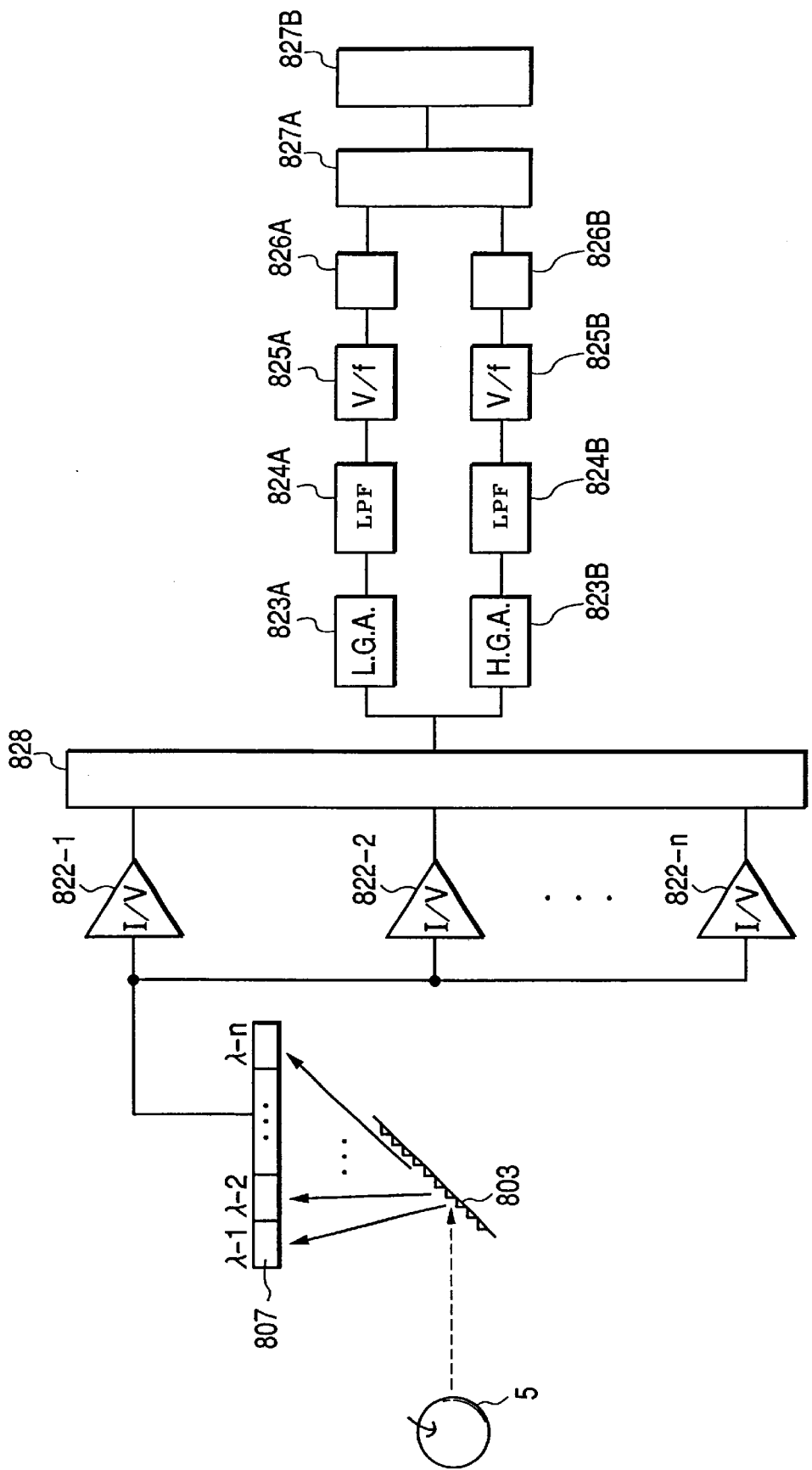
FIG. 10 is a block diagram to illustrate signal processing associated with an eighth embodiment of the present invention.

The seventh embodiment was arranged so that each of the plural split frequency regions had a plurality of amplifying circuits, but this structure is not practical in cases provided with many gain amplifiers and portions coupled as in the present structure, because the total production cost of the received signal processing circuits is increased considerably. In the eighth embodiment of the present invention, as illustrated in the block diagram of the signal processing of FIG. 10, the device is arranged to convert the charge corresponding to each frequency region to a voltage signal by the current-voltage conversion amplifier 822-n and thereafter transmit the voltage signals through multiplexer 828 to two types of gain amplifiers, low and high gain amplifiers 823A, 823B. This presents the same effect as in the second embodiment without a large increase of the production cost. The timing when the multiplexing operation is carried out by the multiplexer 828 is not limited to that in the present embodiment, but it is preferable to take the processing time and cost etc. into consideration and locate it at an appropriate position in the signal processing block according to these.

Although the present embodiment used the photodiodes or the MOS type image sensors as light receiving elements, it should be noted that any photoelectric conversion element can also be applied to the present invention as long as it can convert the intensity of light to a storage amount of charge, a current signal, or a voltage signal. The seventh and eighth embodiments used the diffraction grating for splitting the light of the predetermined frequency region, but it is noted that any optical element can also be applied as long as it has the function to split the light into specific wavelengths.

The intensity data input into the CPU 827B is converted to the internal quality data through the predetermined arithmetic operation and these are displayed in the form of an image on the CRT or the like. The image display may also be of the type of displaying only the propriety of shipping time of inspected object 5 with respect to the reference of a predetermined sugariness. Further, the apparatus may also be arranged to output only the propriety data without the image display and perform the grading of inspected object 5 in the conveyor system continuous from the measurement device.

Execution of the present invention also enables the internal quality analysis of fruits or vegetables having different sizes or different absorbances to be carried out with high accuracy and in short time, based on the stable S/N ratios, by use of the single device.

The structures according to the present invention, described above, permit the received signals obtained to be processed at high speed and with high accuracy. In the practical measurement under continuous conveyance, however, there arises the problem that there occurs a state in which the inspected object 5 is absent between the light source 1 and the light receiving element 2 during the conveyance and as a result the near-infrared light is received directly by the light receiving element 2.

Figure 11:
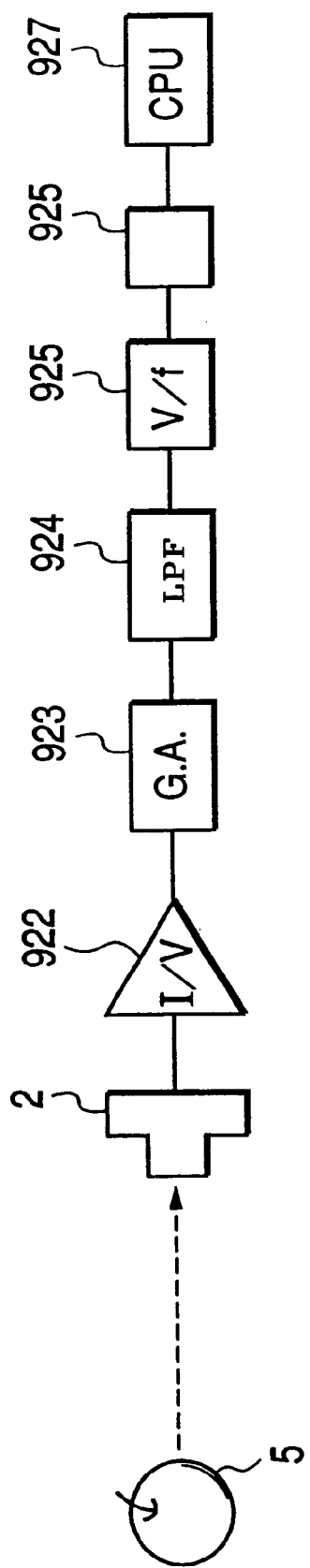
FIG. 11 is a block diagram to illustrate signal processing associated with a ninth embodiment of the present invention.
Figure 12:
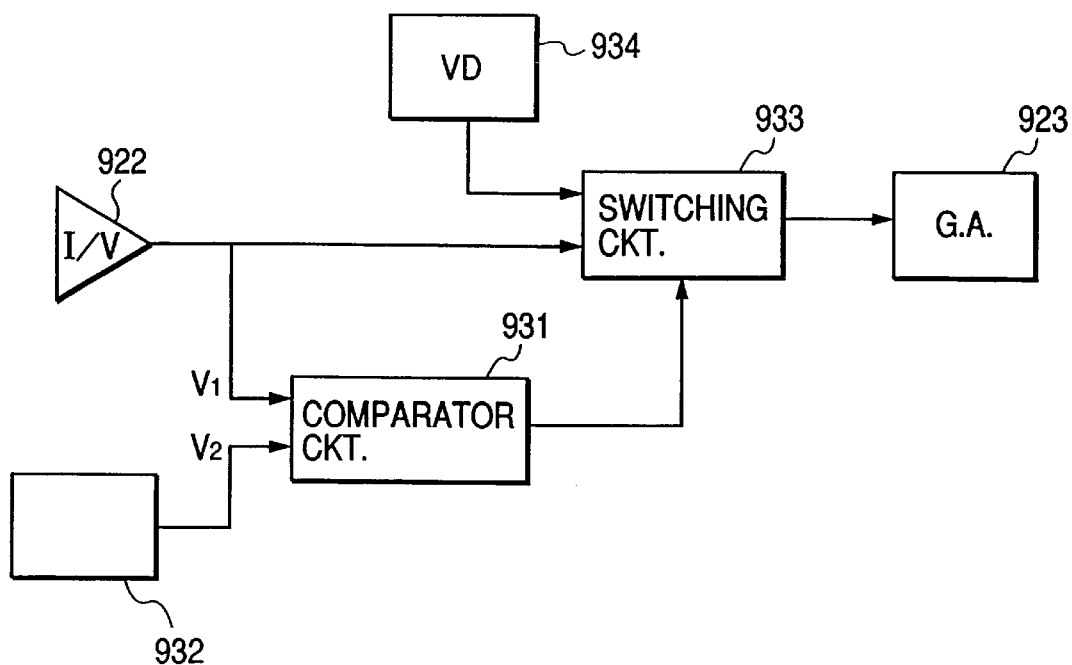
FIG. 12 is a block diagram related to a comparator circuit associated with the ninth embodiment of the present invention.

The ninth embodiment involves the structure as a means for solving the above problem according to the present invention, which is added to the measurement device of internal quality of fruit or vegetable. A block diagram of the signal processing of the ninth embodiment is illustrated in FIG. 11 and a block diagram including a comparator circuit is illustrated in FIG. 12. The present embodiment is not different from the conventional example in the conveyance system 10, the position sensor 11, the light source 1, the photodiode 2, and the signal processing device 12 and in the path in which the near-infrared light (the light having the predetermined frequency region) emitted from the light source 1 toward the inspected object 5 travels through the inspected object 5 and in which the transmitted light is received by the photodiode 2, and the description thereof will be omitted herein. Described below is the signal processing routine after reception of the transmitted light on the photodiode 2 in the present embodiment.

The near-infrared light after split is converted to current by the photodiode 2 and the current is further converted to a voltage signal having a voltage value V1 by the current-voltage conversion amplifier 922. As illustrated in FIG. 12, a comparator circuit 931 compares this voltage value V1 with a voltage value V2 applied from a comparative voltage generating circuit 932.

When the near-infrared light is received directly by the photodiode 2 without any object 5 between the photodiode 2 and the light source 1, very large current appears in the photodiode 2 and is further converted to a voltage signal having an extremely large voltage value V1 by the current-voltage conversion amplifier 922. The comparator circuit 931 compares the voltage value V1 with the voltage value V2, determines that V1≧V2, and makes a voltage signal switching circuit 933 switch the voltage signal applied to the gain amplifier 923 to a voltage Vd equal to a voltage in the initial state, generated by a reference voltage generating circuit 934.

When the near-infrared light is received as the transmitted light by the photodiode 2 with an inspected object 5 being present between the photodiode 2 and the light source 1, the comparator circuit 931 determines that V1<V2 and makes the switching circuit 933 apply the voltage signal having the voltage value of V1 to the gain amplifier 923 as it is. The above operation is carried out during the conveyance of inspected objects 5, whereby occurrence of too large voltage can be avoided in the gain amplifier 923, so as to prevent deviation of initial setting during the calculation of intensity data and degradation of evaluation performance of the evaluation system.

The voltage is amplified by the gain amplifier 923 and thereafter noise components are cut by the low-pass filter 924. Further, the voltage-frequency converter 925 performs conversion of the signal to frequency. After that, the counter 926 counts the frequency during the period of predetermined integration time t. The frequency thus counted is input as the intensity data of the transmitted light received by the photodiode 2, D=f×t, into the CPU 27.

The intensity data input into the CPU 927 is converted to data indicating the internal quality through the predetermined arithmetic operation and these are displayed in the form of an image by the CRT or the like. The image display may also be of the type of displaying only the propriety of shipping of the inspected object 5, for example, with respect to the reference of a predetermined sugariness or the like. Further, the apparatus may also be arranged to output only the propriety data without the image display and perform the grading of inspected object 5 in the conveyance system continuous from the measurement device.

In carrying out the present invention, where there is no fruit or vegetable between the light projecting means and the light receiving means, the voltage signal switching circuit is arranged to send the predetermined reference voltage in the same level as during interception of light, to the amplifying circuit. This can eliminate the occurrence of too large voltage in the evaluation system even in cases where the near-infrared light is projected continuously and the evaluation of internal quality of fruit or vegetable is carried out intermittently. Therefore, the above embodiment can prevent the variation of the base line in measured values and the degradation of evaluation performance.

With the structures described above, the measurement devices of the internal quality of fruit or vegetable according to the present invention can perform the high-speed and high-accuracy quality evaluation for a variety of fruits and vegetables. Further, it is apparent that the structures described above present the outstanding effects when carried out each individually, as described in the first to the ninth embodiments, and they may also be applied in the form of various combinations according to the application including the kind of fruits or vegetables, the permissible time for measurement, etc. or the permissible cost etc. for the evaluation of the quality.

What is claimed is:

1. A measurement device for measuring an internal quality of a fruit or vegetable, which includes:
    conveying means for conveying the fruit or vegetable in a predetermined direction;
    light projecting means for projecting light having a predetermined frequency region toward the fruit or vegetable under conveyance; and
    light receiving means for receiving said light having the predetermined frequency region, having been transmitted by the fruit or vegetable;
    said measurement device comprising:
        frequency region splitting means for splitting the light having the predetermined frequency region, having been transmitted by the fruit or vegetable continuously conveyed on said conveying means, into a predetermined number of frequency regions to guide the light to said light receiving means; and
        a signal processing circuit for converting the transmitted light split into said predetermined number of frequency regions to electric signals at intervals of a predetermined time, integrating the electric signals to convert the signals to intensity data, and converting the intensity data obtained at the intervals of the predetermined time to signals for evaluating the internal quality of the fruit or vegetable,
        wherein said signal processing circuit converts the transmitted light split into the predetermined number of frequency regions to the electric signals substantially simultaneously.

2. A measurement device according to claim 1, wherein said signal processing circuit converts the predetermined number of electric signals to the predetermined number of intensity data simultaneously.

3. A measurement device according to claim 2, wherein said light receiving means includes photoelectric conversion elements.

4. A measurement device according to claim 1, wherein said signal processing circuit converts the predetermined number of electric signals to the predetermined number of intensity data after execution of a multiplexing operation.

5. A measurement device according to claim 1, wherein said light receiving means includes a sensor array comprised of light receiving elements of a charge storage type.

6. A measurement device according to one of claims 1 to 5, further comprising:
    a first memory circuit for storing the predetermined number of intensity data obtained continuously at the intervals of the predetermined time;
    a determination circuit for successively comparing the intensity data stored in said first memory circuit to determine whether the intensity data is to be used as a signal for evaluation; and
    a correction circuit for correcting the intensity data determined as a signal not used for evaluation by said determination circuit, with another intensity data stored in said first memory circuit,
    wherein said signal processing circuit uses the intensity data stored in said first memory circuit and determined as a signal for evaluation by said determination circuit and the intensity data corrected by said correction circuit, as signals for evaluating the internal quality of the fruit or vegetable.

7. A measurement device according to claim 6, wherein the intervals of the predetermined time are not more than 1 msec.

8. A measurement device according to one of claims 1 to 5, further comprising:
    diameter measuring means for measuring a diameter of the fruit or vegetable; and
    a number-of-conversions altering circuit for altering the number of conversions from the transmitted light to the intensity data in said signal processing circuit, according to a result of measurement by said diameter measuring means.

9. A measurement device according to one of claims 1 to 5, wherein said light having the predetermined frequency region is comprised of parallel light and said light receiving means comprises a shield cylinder which is coaxial with said parallel light and which has one open end in contact with said light receiving means and the other open end as close to the fruit or vegetable as possible.

10. A measurement device according to one of claims 1 to 5, wherein said signal processing circuit comprises:
    a plurality of amplifying circuits having different amplification factors according to each electric signal, said amplifying circuits being used for converting the electric signal to the intensity data; and a selection circuit for selecting intensity data amplified within a predetermined range out of a plurality of intensity data obtained using said plurality of amplifying circuits.

11. A measurement device according to one of claims 1 to 5, wherein said signal processing circuit has a comparing circuit for determining whether the electric signal is greater than a predetermined voltage value, and an electric signal switching circuit for applying the electric signal to conversion to the intensity data when the electric signal is smaller than the predetermined voltage value and for applying a predetermined reference electric signal to the conversion to the intensity data when the electric signal is greater than the predetermined voltage value.

12. A measurement device according to one of claims 1 to 5, wherein said signal processing circuit has a comparing circuit for determining whether the electric signal is greater than a predetermined voltage value, and an initializing circuit for applying the electric signal to conversion to the intensity data when the electric signal is smaller than the predetermined voltage value and for stopping the conversion to the intensity data to initialize the signal processing circuit when the electric signal is greater than the predetermined voltage value.

13. A measurement device according to one of claims 1 to 5, wherein said signal processing circuit further comprises:
diameter measuring means for measuring a diameter of the fruit or vegetable, based on the intensity data corresponding to the electric signal, under a decision that the light receiving means is receiving the transmitted light when the electric signal is smaller than a predetermined voltage value; and
a number-of-conversions altering circuit for altering the number of conversions from the transmitted light to the intensity data in said signal processing circuit, according to a result of measurement by said diameter measuring means.

14. A measurement device for measuring an internal quality of a fruit or vegetable, which includes:
conveying means for conveying the fruit or vegetable in a predetermined direction;
light projecting means for projecting light having a predetermined frequency region toward the fruit or vegetable under conveyance; and
light receiving means for receiving said light having the predetermined frequency region, having been transmitted by the fruit or vegetable;
said measurement device comprising:
a signal processing circuit for converting the transmitted light received to electric signals at intervals of a predetermined time, integrating the electric signals to convert the electric signals to intensity data, and converting the intensity data obtained at the intervals of the predetermined time to signals for evaluating the internal quality of the fruit or vegetable;
a first memory circuit for storing the predetermined number of intensity data obtained continuously at the intervals of the predetermined time;
a determination circuit for successively comparing the intensity data stored in said first memory circuit to determine whether the intensity data is to be used as a signal for evaluation; and
a correction circuit for correcting the intensity data determined as a signal not used for evaluation by said determination circuit, using another intensity data stored in said first memory circuit,
wherein said signal processing circuit uses the intensity data stored in said first memory circuit and determined as a signal for evaluation by said determination circuit and the intensity data corrected by said correction circuit, as signals for evaluating the internal quality of the fruit or vegetable.

15. A measurement device according to claim 14, wherein the intervals of the predetermined time are not more than 1 msec.

16. A measurement device according to claim 14 or 15, further comprising:
diameter measuring means for measuring a diameter of the fruit or vegetable; and
a number-of-conversions altering circuit for altering the number of conversions from the transmitted light to the intensity data in said signal processing circuit, according to a result of measurement by said diameter measuring means.

17. A measurement device according to claim 14 or 15, wherein said light having the predetermined frequency region is comprised of parallel light and said light receiving means comprises a shield cylinder which is coaxial with said parallel light and which has one open end in contact with said light receiving means and the other open end as close to the fruit or vegetable as possible.

18. A measurement device for measuring an internal quality of a fruit or vegetable, which includes:
conveying means for conveying the fruit or vegetable in a predetermined direction;
light projecting means for projecting light having a predetermined frequency region toward the fruit or vegetable under conveyance; and
light receiving means for receiving said light having the predetermined frequency region, having been transmitted by the fruit or vegetable;
wherein with the light having said predetermined frequency region, which has been transmitted by the fruit or vegetable conveyed continuously on said conveying means, a signal processing circuit converts the transmitted light received to electric signals at intervals of a predetermined time, integrates the electric signals to convert the electric signals to intensity data, and converts the intensity data obtained at the intervals of the predetermined time to signals for evaluating the internal quality of the fruit or vegetable,
said signal processing circuit comprising:
a plurality of amplifying circuits having different amplification factors according to each electric signal, said amplifying circuits being used for converting the electric signal to the intensity data; and
a selection circuit for selecting intensity data amplified within a predetermined range out of a plurality of intensity data obtained using said plurality of amplifying circuits.

19. A measurement device according to claim 18, wherein said predetermined range is determined based on the intensity data obtained from the transmitted light of a reference wavelength in said predetermined frequency region.

20. A measurement device for measuring an internal quality of a fruit or vegetable, which includes:
conveying means for conveying the fruit or vegetable in a predetermined direction;
light projecting means for projecting light having a predetermined frequency region toward the fruit or vegetable under conveyance; and light receiving means for receiving said light having the predetermined frequency region, having been transmitted by the fruit or vegetable;

said measurement device comprising:
- a signal processing circuit for converting the light having the predetermined frequency region, which has been transmitted by the fruit or vegetable conveyed continuously on said conveying means, to electric signals at intervals of a predetermined time, integrating the electric signals to convert the electric signals to intensity data, and converting the intensity data at the intervals of the predetermined time to signals for evaluating the internal quality of the fruit or vegetable,
- wherein said signal processing circuit comprises a comparing circuit for determining whether the electric signal is greater than a predetermined voltage value, and an electric signal switching circuit for applying the electric signal to conversion to the intensity data when the electric signal is smaller than the predetermined voltage value and for applying a predetermined reference voltage to the conversion to the intensity data when the electric signal is greater than the predetermined voltage value.

21. A measurement device according to claim 20, wherein the light having the predetermined frequency region, which has been transmitted by the fruit or vegetable, is split into a predetermined number of frequency regions by frequency region splitting means and thereafter guided to said light receiving means, and
- wherein said signal processing circuit converts plural beams of the transmitted light split into the predetermined number of frequency regions to electric signals substantially simultaneously.

22. A measurement device according to claim 21, wherein said signal processing circuit converts the predetermined number of electric signals to the predetermined number of intensity data simultaneously.

23. A measurement device according to claim 21, wherein said light receiving means includes photoelectric conversion elements.

24. A measurement device according to claim 21, wherein said signal processing circuit converts the predetermined number of electric signals to the predetermined number of intensity data after execution of a multiplexing operation.

25. A measurement device according to claim 21, wherein said light receiving means includes a sensor array comprised of light receiving elements of a charge storage type.

26. A measurement device according to one of claims 20 to 25, further comprising:
- a first memory circuit for storing the predetermined number of intensity data obtained continuously at the intervals of the predetermined time;
- a determination circuit for successively comparing the intensity data stored in said first memory circuit to determine whether the intensity data is to be used as a signal for evaluation; and
- a correction circuit for correcting the intensity data determined as a signal not used for evaluation by said determination circuit, with another intensity data stored in said first memory circuit,
- wherein said signal processing circuit uses the intensity data stored in said first memory circuit and determined as a signal for evaluation by said determination circuit and the intensity data corrected by said correction circuit, as signals for evaluation the internal quality of the fruit of vegetable.

27. A measurement device according to claim 26, wherein the intervals of the predetermined time are not more than 1 msec.

28. A measurement device according to one of claims 20 to 25, further comprising:
- diameter measuring means for measuring a diameter of the fruit or vegetable; and
- a number-of-conversions altering circuit for altering the number of conversions from the transmitted light to the intensity data in said signal processing circuit, according to a result of measurement by said diameter measuring means.

29. A measurement device according to one of claims 20 to 25, wherein said light having the predetermined frequency region is comprised of parallel light and said light receiving means comprises a shield cylinder which is coaxial with said parallel light and which has one open end in contact with said light receiving means and the other open end as close to the fruit or vegetable as possible.

30. A measurement device according to one of claims 20 to 25, wherein said signal processing circuit comprises:
- a plurality of amplifying circuits having different amplification factors according to each electric signal, said amplifying circuits being used for converting the electric signal to the intensity data; and
- a selection circuit for selecting intensity data amplified within a predetermined range out of a plurality of intensity data obtained using said plurality of amplifying circuits.

31. A measurement device according to claim 4, wherein said light receiving means includes a sensor array comprised of light receiving elements of a charge storage type.

32. A measurement device according to claim 22, wherein said light receiving means includes photoelectric conversion elements.

33. A measurement device according to claim 24, wherein said light receiving means includes a sensor array comprised of light receiving elements of a charge storage type.

34. A measurement device according to claim 26, further comprising:
- diameter measuring means for measuring a diameter of the fruit or vegetable; and
- a number-of-conversions altering circuit for altering the number of conversions from the transmitted light to the intensity data in said signal processing circuit, according to a result of measurement by said diameter measuring means.

35. A measurement device according to claim 26, wherein said signal processing circuit comprises:
- a plurality of amplifying circuits having different amplification factors according to each electric signal, said amplifying circuits being used for converting the electric signal to the intensity data; and
- a selection circuit for selecting the intensity data amplified within a predetermined range out of a plurality of intensity data obtained using said plurality of amplifying circuits.

36. A measurement device according to claim 32 or 33, further comprising:
- a first memory circuit for storing the predetermined number of intensity data obtained continuously at the intervals of the predetermined time;
- a determination circuit for successively comparing the intensity data stored in said first memory circuit to determine whether the intensity data is to be used as a signal for evaluation; and a correction circuit for correcting the intensity data determined as a signal not used for evaluation by said determination circuit, with another intensity data stored in said first memory circuit, wherein said signal processing circuit uses the intensity data stored in said first memory circuit and determined as a signal for evaluation by said determination circuit and the intensity data corrected by said correction circuit, as signals for evaluation the internal quality of the fruit of vegetable.

37. A measurement device according to claim 32 or 33, further comprising:

diameter measuring means for measuring a diameter of the fruit or vegetable; and a number-of-conversions altering circuit for altering the number of conversions from the transmitted light to the intensity data in said signal processing circuit, according to a result of measurement by said diameter measuring means.

38. A measurement device according to claim 32 or 33, wherein said light having the predetermined frequency region is comprised of parallel light and said light receiving means comprises a shield cylinder which is coaxial with said parallel light and which has one open end in contact with said light receiving means and the other open end as close to the fruit or vegetable as possible.

39. A measurement device according to one of claims 32 and 33, wherein said signal processing circuit comprises:

a plurality of amplifying circuits having different amplification factors according to each electric signal, said amplifying circuits being used for converting the electric signal to the intensity data; and a selection circuit for selecting intensity data amplified within a predetermined range out of a plurality of intensity data obtained using said plurality of amplifying circuits.

* * * * *